United States Patent [19]

Tanaka et al.

[11] Patent Number: 4,778,766

[45] Date of Patent: Oct. 18, 1988

[54] METHOD OF TESTING FOR NEUTROPHIL FUNCTION

[75] Inventors: Kuniaki Tanaka; Fumiko Konishi, both of Kurume, Japan

[73] Assignee: Chlorella Industry Co., Ltd., Tokyo, Japan

[21] Appl. No.: 772,735

[22] Filed: Sep. 5, 1985

[30] Foreign Application Priority Data

Sep. 17, 1984 [JP] Japan ................... 59-194426

[51] Int. Cl.$^4$ .................. C12Q 1/68; G01N 1/00; G01N 33/48; A61K 35/78
[52] U.S. Cl. ........................ 436/63; 435/6; 424/2; 424/195.1; 536/1.1
[58] Field of Search .............. 424/195.1, 2; 536/1.1; 436/63; 435/6, 29, 35

[56] References Cited

U.S. PATENT DOCUMENTS 4,331,738  2/1987  Maeda et al. ................ 435/240

FOREIGN PATENT DOCUMENTS 75268 of 1981 Australia .
75269 of 1981 Australia .

OTHER PUBLICATIONS

Chem. Abst. 95: 148665c, 1981.
Chem. Abst. 95: 9365q, 1981.
Chem. Abst. 75: 106387v, 1971.
Chem. Abst. 73: 108241a, 1970.
Chem. Abst. 68: 27703x, 1968.

*Primary Examiner*—John Rollins
*Attorney, Agent, or Firm*—Bacon & Thomas

[57] ABSTRACT

A testing agent for neutrophil function includes a substance having a molecular weight of 5,000 or more. The substance is contained in an extract extracted from chlorella alga using an aqueous solvent. The agent activates neutrophils specifically.

4 Claims, No Drawings

METHOD OF TESTING FOR NEUTROPHIL FUNCTION

BACKGROUND OF THE INVENTION

1. Field of the Invention

The present invention relates to a testing agent for neutrophil function.

2. Description of the Prior Art

Leucocytes for preventing infections in animals are classified into polymorphonuclear leucocytes and mononuclear leucocytes according to their nuclear morphology. Polymorphonuclear leucocytes are further classified into neutrophils, eosinophils and basophils in accordance with the staining of granules. Neutrophils account for about half of the total number of leucocytes.

Neutrophils, as in the case of macrophages, intake foreign substances such as bacteria, i.e., perform ingestion and kill or digest these substances. When these functions of neutrophils are impaired, an organism is easily infected by various bacteria. Typically, these functions are impaired in the disease such as chronic granulomatous disease, Chediak Higashi syndrome and the like. Therefore, when the neutrophil function is tested, the resistance of a subject to an infectious bacterium can be determined and disease caused thereby can be predicted. Further, recent studies in this field show that nutrophils function in the specific immune response.

Conventional neutrophil function testing methods include the following: a testing method wherein heparin-added venous blood is passed through a nylon fiber and afterwards the decreased number of neutrophils is counted; a testing method wherein a bacterium and opsonin are directly added to neutrophils to test the phagocytosis and killing functions; a testing method wherein the metabolism activity upon phagocytosis is determined by utilizing reduction of nitroblue tetrazolium as an index; and a testing method wherein the amount of hydrogen peroxide produced upon phagocytosis is measured. However, only some of various functions of neutrophils can be examined even by these conventional methods which involve complex procedures and require expensive reagents.

SUMMARY OF THE INVENTION

It is an object of the present invention to provide an inexpensive testing agent for the neutrophil function which has a specificity to neutrophils.

In order to achieve the above object of the present invention, there is provided a testing agent for the neutrophil function, comprising a substance contained in an extract extracted from an alga belonging to genus Chlorella and having a molecular weight of 5,000 or more as an effective component.

The testing agent for the neutrophil function according to the present invention has a specificity to normal neutrophils. In other words, although the testing agent of the present invention allows DNA synthesis by normal neutrophils, it does not allow DNA synthesis by neutrophils having a reduced function. Therefore, when a whole sample without lymphocytes or a neutrophil fraction to be tested is treated with a testing agent for neutrophil function according to the present invention, the degree of DNA synthesis by neutrophils in the sample, i.e., the neutrophil function can be tested.

DETAILED DESCRIPTION OF THE PREFERRED EMBODIMENTS

A testing agent for neutrophil function according to the present invention is an agent having as an effective agent a substance of a molecular weight of 5,000 or more which is contained in a chlorella extract.

This substance can be prepared in the following manner. First, chlorella as a raw material is prepared. Any chlorella of the genus Chlorella can be used (e.g., C. vulgaris, C. regularis, C. eripsoidia, etc.). The culture method of an alga of the genus Chlorella is well known. More specifically, a chlorella alga can be cultured by a method requiring sunlight, carbon dioxide gas and various nutrients, i.e., heteroculture. For example, a chlorella alga can be cultured by agitation in an outdoor pool containing acetic acid or glucose as a carbon source, urea or the like as a nitrogen source, and potassium phosphate as a K and P source.

The cultured chlorella alga is subjected to extraction by an aqueous solvent. Before extraction, the alga is preferably spray dried. That is, the alga is sprayed in a hot air flow at 120° C. or higher and dehydrated. Then, the alga is subjected to extraction by an aqueous solvent. The aqueous solvent used contains water, an aqueous solution containing an acid (e.g., 0.2N hydrochloric acid) or a base (e.g., 0.2N sodium hydroxide) having a pH of 5 to 9, and water-containing lower alcohols (e.g., methanol, ethanol). Although the spray-dried alga can be subjected to extraction by the aqueous solvent at 4° to 98° C. for 15 minutes to 1 hour, it is preferably subjected to extraction by the aqueous solvent at 93° to 98° C. for 15 to 40 minutes. The ratio of the alga and aqueous solvent during extraction can be selected to be, for example, 1 g of alga and 20 ml of aqueous solvent. In order to obtain an objective chlorella extract (to be referred to as CE hereinafter), the solvent extract is centrifuged to recover the CE as supernatant.

The thus obtained CE can be directly used as a testing agent for neutrophil function. However, in order to improve the effect as a testing agent, a fraction having a molecular weight of 5,000 or more (to be referred to as CVE-A hereinafter) is preferably recovered from the CE by purification. CVE-A having a molecular weight of 5,000 or more can be obtained by gel filtration chromatography or by dialysis using water. When gel filtration chromatography is performed, well known Sephadex G-25 (trade name) can be used. CVE-A is obtained through this purification process. CVE-A seems to contain various kinds of polysaccharides and proteins.

The CE or CVE-A obtained in this manner is used for testing the function of neutrophils. Before testing, the CE or CVE-A need not be subjected to any treatment. However, the CE or CVE-A as obtained may be lyophilized for purpose of easy handling. The function of neutrophils can be tested by allowing the CE or CVE-A to act on the neutrophils and examining the degree of DNA synthesis. The degree of DNA synthesis of neutrophils can be determined by incubating neutrophils and a marker in the presence of CE or CVE-A and measuring the amount of the marker incorporated into the neutrophils after incubation. The marker can be a radio-labelled nucleoside such as $^{125}$IUdR which is used for synthesis of nucleic acids.

A method of using a testing agent for neutrophil function will be exemplified below in detail. Three milliliters of a liquid having a certain specific gravity for separating lymphocytes (e.g., Ficoll-Hypaque separation medium) are charged into a small test tube, and 2 ml of sample blood diluted with 2 ml of phosphate buffered solution (PBS) (a total of 4 ml) are poured thereover so as not to cause agitation. When the mixture is centrifuged at 400 g for 30 minutes, neutrophils and erythrocytes collect at the bottom of the tube as a precipitate, while lymphocytes, monocytes and platelets collect at an intermediate level in the liquid. Thus, the precipitate is recovered. The precipitate includes neutrophils and erythrocytes. The erythrocytes in the recovered precipitate are hemolyzed by adding an ammonium chloride solution. The separated neutrophils are suspended at a cell concentration of $1 \times 10^5$ to $5 \times 10^6$ cells/ml, and normally $5 \times 10^5$ cells/ml, using PRMI1640 as a culture medium. 100 μl of the neutrophil suspension are mixed with 100 μl of a solution obtained by dissolving 10 to 100 μl of lyophilized CE or CVE-A per ml of RPMI1640. The resultant mixture is incubated in a carbon dioxide gas incubator at 37° C. for 1 hour. After addition of 20 μl of $^{125}$IUdR solution prepared to have a concentration of 50 μCi/ml with RPMI1640, the mixture is incubated for another 3 to 6 hours and the amount of $^{125}$IUdR incorporated by the neutrophils is measured.

EXAMPLE 1

Preparation of Testing Agent for Neutrophil Function

Chlorella vulgaris was cultured by conventional heteroculture. The culture was performed under agitation in an outdoor pool using acetic acid or glucose as a carbon source, urea or the like as a nitrogen source, and potassium phosphate as a K and P source. The collected chlorella alga was spray-dried in a hot air flow at 120° C. or more. One gram of the dried chlorella alga was placed in 20 ml of water at 93° C. and was heated within a temperature range of 93° to 98° C. for 15 minutes under frequent agitation. Thereafter, the water containing the alga was cooled to 4° C., and centrifuged at 6,000 rpm for 15 minutes. The supernatant was recovered to obtain CE. The CE was gelfiltrated with Sephadex G-25 (trade name) to obtain a fraction (CVE-A) having a molecular weight of 5,000 or more.

EXAMPLE 2

Activation of Neutrophils by CVE-A

Human peripheral blood was sampled, and neutrophils were separated from the sample blood by a method using a Ficoll-Hypaque separation medium as described above. A mixture of 0.1 ml of a suspension having a cell concentration of $5 \times 10^5$ per ml of RPMI1640 (N.B.) with 1.0 ml of a solution containing 30 μg of lyophilized CVE-A per ml of RPMI1640 was prepared. The mixture was incubated at 37° C. for 1 hour. After one μCi of $^{125}$IUdR was added to the mixture and incubation was performed at 37° C. for another 3 hours, the amount of $^{125}$IUdR incorporated by the neutrophils was measured by a gamma scintillation counter. As a control, the amount of $^{125}$IUdR incorporated by a sample prepared by the same method but without adding CVE-A was also measured. The sample with the CVE-A added has a 125IUdR amount of $2210 \pm 101$ cpm while the control sample had a 125I-UdR amount of $843 \pm 23$ cpm. These results reveal the CVE-A facilitates DNA syntheis of neutrophils and specifically activates neutrophils. (N.B.)

| Composition of RPMI1640 Medium | (mg/ml) |
| --- | --- |
| L-arginine.HCl | 200 |
| L-asparagine | 50.0 |
| L-aspartic acid | 20.0 |
| C-cysteine | 50.0 |
| L-glutamine | 300 |
| L-glutamic acid | 20.0 |
| Glycine | 10.0 |
| L-histidine.HCl | 15.0 |
| Hydroxy-L-prorine | 20.0 |
| L-leucine | 50.0 |
| L-isoleucine | 50.0 |
| L-lysine.HCl | 40.0 |
| L-methionine | 15.0 |
| L-phenylalanine | 15.0 |
| L-proline | 20.0 |
| L-serine | 30.0 |
| L-threonine | 20.0 |
| L-tryptophan | 5.0 |
| L-tyrosine | 20.0 |
| L-varine | 20.0 |
| L-paraminobenzoate | 1.0 |
| Biotin | 0.2 |
| Calcium pantothenate | 0.25 |
| Choline chloride | 3.0 |
| Folic acid | 1.0 |
| Inositol | 35.0 |
| Nicotinamide | 1.0 |
| Pyridoxal.HCl | 1.0 |
| Riboflavin | 0.2 |
| Thiamine.HCl | 1.0 |
| Vitamin B12 | 0.005 |
| Glucose | 2000 |
| Glutathione | 1.0 |
| NaCl | 6000 |
| KCl | 400 |
| $MgSo_4.7H_2O$ | 100 |
| $Na_2HPO_4.7H_2O$ | 1512 |
| $Ca(NO_3)_2.4H_2O$ | 100 |
| Phenol red | 5.0 |

What is claimed is:

1. A method of testing for impaired neutrophils in animals which comprises obtaining from an animal to be tested a blood sample and preparing the sample to be without lymphocytes or obtaining a neutrophil fraction thereof, culturing said treated sample or fraction in a culturing medium to which is added a testing agent comprising as an effective component a substance having a molecular weight not less than 5,000 contained in an extract extracted from a chlorella alga by an aqueous solvent and wherein the agent activates DNA synthesis in normal neutrophils and does not activate DNA synthesis in neutrophils having a reduced function and a marker for DNA synthesis, measuring the amount of marker incorporated into the neutrophils and comparing this amount with the amount incorporated in a control which does not contain the testing agent to determine if there is a larger amount of marker in the tested sample than in the control.

2. A method according to claim 1 wherein the marker is $^{125}$UIdR.

3. A method of testing for impaired neutrophils in animals which comprises obtaining from an animal to be tested a blood sample and preparing the sample to be without lymphocytes or obtaining a neutrophil fraction thereof, culturing said treated sample or fraction in a culturing medium to which is added a testing agent comprising as an effective component a substance having a molecular weight not less than 5,000 which is obtained by extraction of a chlorella alga by an aqueous solvent and purified by gelfiltration chromatography or dialysis against water and wherein the agent activates DNA synthesis in normal nuetrophils and does not activate DNA synthesis in neutrophils having a reduced function and a marker for DNA synthesis, measuring the amount of marker incorporated into the neutrophils and comparing this amount with the amount incorporated in a control which does not contain the testing agent to determine if there is a larger amount of marker in the tested sample than in the control.

4. A method according to claim 3 wherein the marker is $^{125}$IUdR.

* * * * *